(12) United States Patent
Pett et al.

(10) Patent No.: US 12,390,229 B2
(45) Date of Patent: Aug. 19, 2025

(54) INTRAOSSEOUS MODULAR POWER

(71) Applicant: Bard Access Systems, Inc., Salt Lake City, UT (US)

(72) Inventors: Daniel Pett, Sandy, UT (US); Jason Edie, Sandy, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 18/599,077

(22) Filed: Mar. 7, 2024

(65) Prior Publication Data

US 2024/0206887 A1 Jun. 27, 2024

Related U.S. Application Data

(63) Continuation of application No. 17/667,291, filed on Feb. 8, 2022, now Pat. No. 11,925,361.
(Continued)

(51) Int. Cl.
*A61B 17/16* (2006.01)
*A61B 10/02* (2006.01)
(Continued)

(52) U.S. Cl.
CPC ...... *A61B 17/1628* (2013.01); *A61B 17/1637* (2013.01); *A61B 17/3472* (2013.01);
(Continued)

(58) Field of Classification Search
CPC ............ A61B 17/1628; A61B 17/1637; A61B 17/3472; A61B 2010/0258; H02J 7/0042; H02J 2207/20
See application file for complete search history.

(56) References Cited

U.S. PATENT DOCUMENTS

| | | | |
|---|---|---|---|
| 2,773,501 | A | 12/1956 | Young |
| 3,071,135 | A | 1/1963 | Baldwin et al. |

(Continued)

FOREIGN PATENT DOCUMENTS

| | | | |
|---|---|---|---|
| CN | 108742795 | A | 11/2018 |
| CN | 110547847 | A | 12/2019 |

(Continued)

OTHER PUBLICATIONS

PCT/US2024/014241 filed Feb. 2, 2024 International Search Report and Written Opinion dated May 8, 2024.
(Continued)

*Primary Examiner* — Zade Coley
*Assistant Examiner* — Diana Jones
(74) *Attorney, Agent, or Firm* — Rutan & Tucker LLP (57) ABSTRACT

An intraosseous access system, including a needle configured to drill into bone via rotation of the needle, and a driver. The driver can be configured to impart rotational power to the needle. The driver can include a power converter and a first power source connected to the power converter. The system can further include a second power source external to the driver and selectively connectable to the driver. A method of drilling through a bone includes providing the intraosseous access system, applying rotational power to the needle, and placing the needle in contact with the bone. The method can further include coupling the second power source to the power converter so that power from the second power source is combined with power from the first energy source.

16 Claims, 5 Drawing Sheets

Related U.S. Application Data (60) Provisional application No. 63/147,119, filed on Feb. 8, 2021.

(51) Int. Cl.
*A61B 17/34* (2006.01)
*H02J 7/00* (2006.01)

(52) U.S. Cl.
CPC ..... *H02J 7/0042* (2013.01); *A61B 2010/0258* (2013.01); *H02J 2207/20* (2020.01)

(56) References Cited

U.S. PATENT DOCUMENTS

| | | |
|---|---|---|
| 3,261,594 A | 7/1966 | Michel |
| 3,734,207 A | 5/1973 | Fishbein |
| 3,753,432 A | 8/1973 | Guerra |
| 3,804,544 A | 4/1974 | Adams |
| 3,811,442 A | 5/1974 | Maroth |
| 3,815,605 A | 6/1974 | Schmidt et al. |
| 3,991,765 A | 11/1976 | Cohen |
| 4,266,555 A | 5/1981 | Jamshidi |
| 4,314,565 A | 2/1982 | Lee |
| 4,342,724 A | 8/1982 | Narra |
| 4,381,777 A | 5/1983 | Garnier |
| 4,383,530 A | 5/1983 | Bruno |
| 4,562,844 A | 1/1986 | Carpenter et al. |
| 4,736,742 A | 4/1988 | Alexson et al. |
| 4,787,893 A | 11/1988 | Villette |
| 4,889,529 A | 12/1989 | Haindl |
| 4,952,207 A | 8/1990 | Lemieux |
| 4,964,854 A | 10/1990 | Luther |
| 4,969,870 A | 11/1990 | Kramer et al. |
| 5,040,542 A | 8/1991 | Gray |
| 5,042,558 A | 8/1991 | Hussey et al. |
| 5,053,017 A | 10/1991 | Chamuel |
| 5,122,114 A | 6/1992 | Miller et al. |
| 5,207,697 A | 5/1993 | Carusillo et al. |
| 5,263,939 A | 11/1993 | Wortrich |
| 5,290,267 A | 3/1994 | Zimmermann |
| 5,312,364 A | 5/1994 | Jacobs |
| 5,332,398 A | 7/1994 | Miller et al. |
| 5,364,367 A | 11/1994 | Banks et al. |
| 5,372,583 A | 12/1994 | Roberts et al. |
| 5,384,103 A | 1/1995 | Miller |
| 5,406,940 A | 4/1995 | Melzer et al. |
| 5,451,210 A | 9/1995 | Kramer et al. |
| 5,554,154 A | 9/1996 | Rosenberg |
| 5,573,358 A | 11/1996 | Gobbers et al. |
| 5,575,780 A | 11/1996 | Saito |
| 5,591,188 A | 1/1997 | Waisman |
| 5,601,559 A | 2/1997 | Melker et al. |
| 5,667,509 A | 9/1997 | Westin |
| 5,688,249 A | 11/1997 | Chang et al. |
| 5,694,019 A | 12/1997 | Uchida et al. |
| 5,779,708 A | 7/1998 | Wu |
| 5,817,052 A | 10/1998 | Johnson et al. |
| 5,853,393 A | 12/1998 | Bogert |
| 5,868,711 A | 2/1999 | Kramer et al. |
| 5,885,293 A | 3/1999 | McDevitt |
| 5,927,976 A | 7/1999 | Wu |
| 5,960,797 A | 10/1999 | Kramer et al. |
| 5,967,143 A | 10/1999 | Klappenberger |
| 6,018,227 A | 1/2000 | Kumar et al. |
| 6,056,165 A | 5/2000 | Speranza |
| 6,104,162 A | 8/2000 | Sainsbury et al. |
| 6,117,108 A | 9/2000 | Woehr et al. |
| 6,135,769 A | 10/2000 | Kwan |
| 6,159,161 A | 12/2000 | Hodosh |
| 6,199,664 B1 | 3/2001 | Tkaczyk et al. |
| 6,210,373 B1 | 4/2001 | Allmon |
| 6,228,088 B1 | 5/2001 | Miller et al. |
| 6,247,928 B1 | 6/2001 | Meller et al. |
| 6,270,484 B1 | 8/2001 | Yoon |
| 6,273,715 B1 | 8/2001 | Meller et al. |
| 6,419,490 B1 | 7/2002 | Kitchings Weathers, Jr. |
| 6,458,117 B1 | 10/2002 | Pollins, Sr. |
| 6,527,778 B2 | 3/2003 | Athanasiou et al. |
| 6,547,561 B2 | 4/2003 | Meller et al. |
| 6,602,214 B2 | 8/2003 | Heinz et al. |
| 6,626,887 B1 | 9/2003 | Wu |
| 6,629,959 B2 | 10/2003 | Kuracina et al. |
| 6,641,395 B2 | 11/2003 | Kumar et al. |
| 6,652,490 B2 | 11/2003 | Howell |
| 6,692,471 B2 | 2/2004 | Boudreaux |
| 6,715,969 B2 | 4/2004 | Eriksen |
| 6,761,726 B1 | 7/2004 | Findlay et al. |
| 6,814,734 B2 | 11/2004 | Chappuis et al. |
| 6,830,562 B2 | 12/2004 | Mogensen et al. |
| 6,875,219 B2 | 4/2005 | Arramon et al. |
| 6,905,486 B2 | 6/2005 | Gibbs |
| 6,916,292 B2 | 7/2005 | Morawski et al. |
| 6,984,213 B2 | 1/2006 | Horner et al. |
| 6,997,907 B2 | 2/2006 | Safabash et al. |
| 7,112,191 B2 | 9/2006 | Daga |
| 7,135,031 B2 | 11/2006 | Flint |
| 7,214,208 B2 | 5/2007 | Vaillancourt et al. |
| 7,347,838 B2 | 3/2008 | Kulli |
| 7,347,840 B2 | 3/2008 | Findlay et al. |
| 7,407,493 B2 | 8/2008 | Cane' |
| 7,458,954 B2 | 12/2008 | Ferguson et al. |
| 7,513,888 B2 | 4/2009 | Sircom et al. |
| 7,530,965 B2 | 5/2009 | Villa et al. |
| 7,534,227 B2 | 5/2009 | Kulli |
| 7,569,033 B2 | 8/2009 | Greene et al. |
| 7,582,102 B2 | 9/2009 | Heinz et al. |
| 7,588,559 B2 | 9/2009 | Aravena et al. |
| 7,658,725 B2 | 2/2010 | Bialecki et al. |
| 7,670,328 B2 | 3/2010 | Miller |
| 7,699,807 B2 | 4/2010 | Faust et al. |
| 7,699,850 B2 | 4/2010 | Miller |
| 7,736,332 B2 | 6/2010 | Carlyon et al. |
| 7,749,225 B2 | 7/2010 | Chappuis et al. |
| 7,798,994 B2 | 9/2010 | Brimhall |
| 7,811,260 B2 | 10/2010 | Miller et al. |
| 7,815,642 B2 | 10/2010 | Miller |
| 7,828,774 B2 | 11/2010 | Harding et al. |
| 7,833,204 B2 | 11/2010 | Picha |
| 7,842,038 B2 | 11/2010 | Haddock et al. |
| 7,850,620 B2 | 12/2010 | Miller et al. |
| 7,850,650 B2 | 12/2010 | Breitweiser |
| D633,199 S | 2/2011 | MacKay et al. |
| 7,899,528 B2 | 3/2011 | Miller et al. |
| 7,905,857 B2 | 3/2011 | Swisher |
| 7,951,089 B2 | 5/2011 | Miller |
| 7,955,297 B2 | 6/2011 | Radmer et al. |
| 7,972,339 B2 | 7/2011 | Nassiri et al. |
| 7,976,502 B2 | 7/2011 | Baid |
| 8,038,038 B2 | 10/2011 | Hillhouse et al. |
| 8,038,664 B2 | 10/2011 | Miller et al. |
| 8,043,253 B2 | 10/2011 | Kraft et al. |
| 8,043,265 B2 | 10/2011 | Abe et al. |
| 8,142,365 B2 | 3/2012 | Miller |
| 8,152,771 B2 | 4/2012 | Mogensen et al. |
| 8,162,904 B2 | 4/2012 | Takano et al. |
| 8,167,899 B2 | 5/2012 | Justis et al. |
| 8,221,398 B2 | 7/2012 | Isobe et al. |
| 8,235,945 B2 | 8/2012 | Baid |
| 8,246,584 B2 | 8/2012 | Aravena et al. |
| 8,273,053 B2 | 9/2012 | Saltzstein |
| 8,292,891 B2 | 10/2012 | Browne et al. |
| 8,308,693 B2 | 11/2012 | Miller et al. |
| 8,333,769 B2 | 12/2012 | Browne et al. |
| 8,356,598 B2 | 1/2013 | Rumsey |
| 8,357,163 B2 | 1/2013 | Sidebotham et al. |
| 8,388,541 B2 | 3/2013 | Messerly et al. |
| 8,388,623 B2 | 3/2013 | Browne et al. |
| 8,414,539 B1 | 4/2013 | Kuracina et al. |
| 8,419,683 B2 | 4/2013 | Miller et al. |
| 8,480,632 B2 | 7/2013 | Miller et al. |
| 8,480,672 B2 | 7/2013 | Browne et al. |
| 8,486,027 B2 | 7/2013 | Findlay et al. |
| 8,506,568 B2 | 8/2013 | Miller |
| 8,535,271 B2 | 9/2013 | Fuchs et al. |

(56) References Cited

U.S. PATENT DOCUMENTS

| | | |
|---|---|---|
| 8,562,615 B2 | 10/2013 | Browne et al. |
| 8,615,286 B2 | 12/2013 | Shen et al. |
| 8,641,715 B2 | 2/2014 | Miller |
| 8,647,257 B2 | 2/2014 | Jansen et al. |
| 8,656,929 B2 | 2/2014 | Miller et al. |
| 8,657,790 B2 | 2/2014 | Tal et al. |
| 8,663,231 B2 | 3/2014 | Browne et al. |
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 8,771,230 B2 | 7/2014 | White et al. |
| 8,781,555 B2 | 7/2014 | Burnside et al. |
| 8,801,663 B2 | 8/2014 | Woehr |
| 8,812,101 B2 | 8/2014 | Miller et al. |
| 8,814,835 B2 | 8/2014 | Baid |
| 8,821,493 B2 | 9/2014 | Anderson |
| 8,828,001 B2 | 9/2014 | Stearns et al. |
| 8,849,382 B2 | 9/2014 | Cox et al. |
| 8,870,872 B2 | 10/2014 | Miller |
| 8,894,654 B2 | 11/2014 | Anderson |
| 8,936,575 B2 | 1/2015 | Moulton |
| 8,944,069 B2 | 2/2015 | Miller et al. |
| 8,974,410 B2 | 3/2015 | Miller et al. |
| 8,998,848 B2 | 4/2015 | Miller et al. |
| 9,072,543 B2 | 7/2015 | Miller et al. |
| 9,078,637 B2 | 7/2015 | Miller |
| 9,149,625 B2 | 10/2015 | Woehr et al. |
| 9,161,798 B2 | 10/2015 | Truckai et al. |
| 9,173,679 B2 | 11/2015 | Tzachar et al. |
| 9,226,756 B2 | 1/2016 | Teisen et al. |
| 9,278,195 B2 | 3/2016 | Erskine |
| 9,295,487 B2 | 3/2016 | Miller et al. |
| 9,302,077 B2 | 4/2016 | Domonkos et al. |
| 9,314,232 B2 | 4/2016 | Stark |
| 9,314,270 B2 | 4/2016 | Miller |
| 9,358,348 B2 | 6/2016 | Weilbacher et al. |
| 9,393,031 B2 | 7/2016 | Miller |
| 9,414,815 B2 | 8/2016 | Miller et al. |
| 9,415,192 B2 | 8/2016 | Kuracina et al. |
| 9,421,345 B2 | 8/2016 | Woehr et al. |
| 9,427,555 B2 | 8/2016 | Baid |
| 9,433,400 B2 | 9/2016 | Miller |
| 9,439,667 B2 | 9/2016 | Miller |
| 9,439,702 B2 | 9/2016 | Arthur et al. |
| 9,445,743 B2 | 9/2016 | Kassab |
| 9,451,968 B2 | 9/2016 | Miller et al. |
| 9,451,983 B2 | 9/2016 | Windolf |
| 9,456,766 B2 | 10/2016 | Cox et al. |
| 9,480,483 B2 | 11/2016 | Browne et al. |
| 9,492,097 B2 | 11/2016 | Wilkes et al. |
| 9,504,477 B2 | 11/2016 | Miller et al. |
| 9,521,961 B2 | 12/2016 | Silverstein et al. |
| 9,545,243 B2 | 1/2017 | Miller et al. |
| 9,554,716 B2 | 1/2017 | Burnside et al. |
| 9,615,816 B2 | 4/2017 | Woodard |
| 9,615,838 B2 | 4/2017 | Nino et al. |
| 9,623,210 B2 | 4/2017 | Woehr |
| 9,636,031 B2 | 5/2017 | Cox |
| 9,636,484 B2 | 5/2017 | Baid |
| 9,649,048 B2 | 5/2017 | Cox et al. |
| 9,681,889 B1 | 6/2017 | Greenhalgh et al. |
| 9,687,633 B2 | 6/2017 | Teoh |
| 9,717,564 B2 | 8/2017 | Miller et al. |
| 9,730,729 B2 | 8/2017 | Kilcoin et al. |
| 9,782,546 B2 | 10/2017 | Woehr |
| 9,839,740 B2 | 12/2017 | Beamer et al. |
| 9,844,646 B2 | 12/2017 | Knutsson |
| 9,844,647 B2 | 12/2017 | Knutsson |
| 9,872,703 B2 | 1/2018 | Miller et al. |
| 9,883,853 B2 | 2/2018 | Woodard et al. |
| 9,895,512 B2 | 2/2018 | Kraft et al. |
| 9,962,211 B2 | 5/2018 | Csernatoni |
| 10,052,111 B2 | 8/2018 | Miller et al. |
| 10,092,320 B2 | 10/2018 | Morgan et al. |
| 10,092,706 B2 | 10/2018 | Denzer et al. |
| 10,159,531 B2 | 12/2018 | Misener et al. |
| 10,172,538 B2 | 1/2019 | Kassab |
| 10,413,211 B2 | 9/2019 | Kassab |
| 10,449,330 B2 | 10/2019 | Newman et al. |
| D898,908 S | 10/2020 | Denzer et al. |
| 10,893,887 B2 | 1/2021 | Blanchard |
| 10,973,532 B2 | 4/2021 | Miller et al. |
| 10,973,545 B2 | 4/2021 | Miller et al. |
| 10,980,522 B2 | 4/2021 | Muse |
| 11,298,202 B2 | 4/2022 | Miller et al. |
| 11,446,112 B2 | 9/2022 | Fink et al. |
| 11,896,264 B2 | 2/2024 | Lindekugel et al. |
| 11,925,361 B2 * | 3/2024 | Pett ............... A61B 17/3472 |
| 11,998,237 B2 | 6/2024 | Lindekugel et al. |
| 12,274,469 B2 | 4/2025 | Pett |
| 2003/0060781 A1 | 3/2003 | Mogensen et al. |
| 2003/0225344 A1 | 12/2003 | Miller |
| 2003/0225411 A1 | 12/2003 | Miller |
| 2003/0229308 A1 | 12/2003 | Tsals et al. |
| 2004/0010236 A1 | 1/2004 | Morawski et al. |
| 2004/0059317 A1 | 3/2004 | Hermann |
| 2004/0220497 A1 | 11/2004 | Findlay et al. |
| 2004/0243135 A1 | 12/2004 | Koseki |
| 2005/0035014 A1 | 2/2005 | Cane |
| 2005/0101912 A1 | 5/2005 | Faust et al. |
| 2005/0113866 A1 | 5/2005 | Heinz et al. |
| 2005/0131345 A1 | 6/2005 | Miller |
| 2005/0165403 A1 | 7/2005 | Miller |
| 2006/0015066 A1 | 1/2006 | Turieo et al. |
| 2006/0020191 A1 | 1/2006 | Brister et al. |
| 2006/0025723 A1 | 2/2006 | Ballarini |
| 2006/0058826 A1 | 3/2006 | Evans et al. |
| 2006/0147283 A1 | 7/2006 | Phillips |
| 2007/0049945 A1 | 3/2007 | Miller |
| 2007/0096690 A1 | 5/2007 | Casalena et al. |
| 2007/0098507 A1 | 5/2007 | Whitehead |
| 2007/0151116 A1 | 7/2007 | Malandain |
| 2007/0191772 A1 | 8/2007 | Wojcik |
| 2007/0270775 A1 | 11/2007 | Miller et al. |
| 2007/0276352 A1 | 11/2007 | Crocker et al. |
| 2007/0282344 A1 | 12/2007 | Yedlicka et al. |
| 2008/0015467 A1 | 1/2008 | Miller |
| 2008/0154304 A1 | 6/2008 | Crawford et al. |
| 2008/0208136 A1 | 8/2008 | Findlay et al. |
| 2008/0215056 A1 * | 9/2008 | Miller ............... A61B 17/32002 606/80 |
| 2008/0221580 A1 * | 9/2008 | Miller ............... A61B 17/1622 606/80 |
| 2008/0257359 A1 | 10/2008 | Rumsey |
| 2009/0000292 A1 * | 1/2009 | Schifferer ............ B66F 17/003 702/41 |
| 2009/0022557 A1 | 1/2009 | Whitehead |
| 2009/0048575 A1 | 2/2009 | Waters |
| 2009/0054808 A1 | 2/2009 | Miller |
| 2009/0093830 A1 | 4/2009 | Miller |
| 2009/0194446 A1 | 8/2009 | Miller et al. |
| 2009/0204024 A1 | 8/2009 | Miller |
| 2009/0306697 A1 | 12/2009 | Fischvogt |
| 2010/0004606 A1 | 1/2010 | Hansen et al. |
| 2010/0174243 A1 | 7/2010 | McKay |
| 2010/0202842 A1 | 8/2010 | Whitehead et al. |
| 2010/0204649 A1 | 8/2010 | Miller et al. |
| 2010/0286607 A1 | 11/2010 | Saltzstein |
| 2010/0298830 A1 | 11/2010 | Browne et al. |
| 2010/0298831 A1 | 11/2010 | Browne et al. |
| 2010/0312246 A1 | 12/2010 | Browne et al. |
| 2011/0004163 A1 | 1/2011 | Vaidya |
| 2011/0028976 A1 | 2/2011 | Miller |
| 2011/0202065 A1 | 8/2011 | Takizawa et al. |
| 2012/0116390 A1 | 5/2012 | Madan |
| 2012/0116394 A1 | 5/2012 | Timm et al. |
| 2012/0202180 A1 | 8/2012 | Stock et al. |
| 2012/0203154 A1 | 8/2012 | Tzachar |
| 2012/0274280 A1 | 11/2012 | Yip et al. |
| 2013/0030439 A1 | 1/2013 | Browne et al. |
| 2013/0041345 A1 | 2/2013 | Kilcoin et al. |
| 2013/0072938 A1 | 3/2013 | Browne et al. |
| 2013/0102924 A1 | 4/2013 | Findlay et al. |

(56) References Cited

U.S. PATENT DOCUMENTS

| | | |
|---|---|---|
| 2013/0158484 A1 | 6/2013 | Browne et al. |
| 2013/0178807 A1 | 7/2013 | Baid |
| 2014/0031674 A1 | 1/2014 | Newman et al. |
| 2014/0031794 A1 | 1/2014 | Windolf |
| 2014/0039400 A1 | 2/2014 | Browne et al. |
| 2014/0081281 A1 | 3/2014 | Felder |
| 2014/0142577 A1 | 5/2014 | Miller |
| 2014/0171873 A1 | 6/2014 | Mark |
| 2014/0188133 A1 | 7/2014 | Misener |
| 2014/0221970 A1 | 8/2014 | Eaton et al. |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward et al. |
| 2014/0276471 A1 | 9/2014 | Emery et al. |
| 2014/0276833 A1 | 9/2014 | Larsen et al. |
| 2014/0276839 A1* | 9/2014 | Forman .............. A61B 17/1622 173/2 |
| 2014/0343454 A1 | 11/2014 | Miller et al. |
| 2014/0343497 A1 | 11/2014 | Baid |
| 2015/0011941 A1 | 1/2015 | Saeki |
| 2015/0025311 A1 | 1/2015 | Kadan et al. |
| 2015/0045732 A1 | 2/2015 | Murphy et al. |
| 2015/0080762 A1 | 3/2015 | Kassab et al. |
| 2015/0126931 A1 | 5/2015 | Holm et al. |
| 2015/0196737 A1 | 7/2015 | Baid |
| 2015/0223786 A1 | 8/2015 | Morgan et al. |
| 2015/0230823 A1 | 8/2015 | Morgan et al. |
| 2015/0238733 A1 | 8/2015 | bin Abdulla |
| 2015/0342615 A1 | 12/2015 | Keinan et al. |
| 2015/0342756 A1 | 12/2015 | Bays et al. |
| 2015/0351797 A1 | 12/2015 | Miller et al. |
| 2015/0366569 A1 | 12/2015 | Miller |
| 2015/0367487 A1 | 12/2015 | Nino et al. |
| 2016/0009812 A1 | 1/2016 | Satelli et al. |
| 2016/0022282 A1 | 1/2016 | Miller et al. |
| 2016/0022284 A1 | 1/2016 | Lele et al. |
| 2016/0039916 A1 | 2/2016 | Jiang et al. |
| 2016/0058432 A1 | 3/2016 | Miller |
| 2016/0066954 A1 | 3/2016 | Miller et al. |
| 2016/0136410 A1 | 5/2016 | Aklog et al. |
| 2016/0183974 A1 | 6/2016 | Miller |
| 2016/0184509 A1 | 6/2016 | Miller et al. |
| 2016/0235949 A1 | 8/2016 | Baid |
| 2016/0305497 A1 | 10/2016 | Victor et al. |
| 2016/0354539 A1 | 12/2016 | Tan et al. |
| 2016/0361519 A1 | 12/2016 | Teoh et al. |
| 2017/0020533 A1 | 1/2017 | Browne et al. |
| 2017/0020560 A1 | 1/2017 | Van Citters et al. |
| 2017/0021138 A1 | 1/2017 | Sokolski |
| 2017/0043135 A1 | 2/2017 | Knutsson |
| 2017/0105763 A1 | 4/2017 | Karve et al. |
| 2017/0136217 A1 | 5/2017 | Riesenberger et al. |
| 2017/0151419 A1 | 6/2017 | Sonksen |
| 2017/0156740 A9 | 6/2017 | Stark |
| 2017/0156751 A1 | 6/2017 | Csernatoni |
| 2017/0209129 A1 | 7/2017 | Fagundes et al. |
| 2017/0231644 A1 | 8/2017 | Anderson |
| 2017/0303962 A1 | 10/2017 | Browne et al. |
| 2017/0303963 A1 | 10/2017 | Kilcoin et al. |
| 2018/0049772 A1 | 2/2018 | Brockman et al. |
| 2018/0092662 A1 | 4/2018 | Rioux et al. |
| 2018/0116551 A1 | 5/2018 | Newman et al. |
| 2018/0116642 A1 | 5/2018 | Woodard et al. |
| 2018/0116693 A1 | 5/2018 | Blanchard et al. |
| 2018/0117262 A1 | 5/2018 | Islam |
| 2018/0125465 A1 | 5/2018 | Muse et al. |
| 2018/0153474 A1 | 6/2018 | Aeschlimann et al. |
| 2018/0154112 A1 | 6/2018 | Chan et al. |
| 2018/0221003 A1 | 8/2018 | Hibner et al. |
| 2018/0228509 A1 | 8/2018 | Fojtik |
| 2018/0242982 A1 | 8/2018 | Laughlin et al. |
| 2019/0009398 A1 | 1/2019 | Zhong et al. |
| 2019/0030701 A1 | 1/2019 | Duggan |
| 2019/0059986 A1 | 2/2019 | Shelton, IV et al. |
| 2019/0069812 A1 | 3/2019 | Isaacson et al. |
| 2019/0083753 A1 | 3/2019 | Chu |
| 2019/0150954 A1 | 5/2019 | Xie |
| 2019/0175220 A1 | 6/2019 | Coppedge et al. |
| 2019/0282244 A1 | 9/2019 | Muse |
| 2020/0054347 A1 | 2/2020 | Coppedge et al. |
| 2020/0054410 A1 | 2/2020 | Pfotenhauer et al. |
| 2020/0113584 A1 | 4/2020 | McGinley et al. |
| 2020/0129186 A1 | 4/2020 | Miller et al. |
| 2020/0197121 A1 | 6/2020 | Morey et al. |
| 2020/0297382 A1 | 9/2020 | Coppedge et al. |
| 2020/0297452 A1 | 9/2020 | Coppedge et al. |
| 2020/0337782 A1 | 10/2020 | Glassman et al. |
| 2021/0015529 A1 | 1/2021 | Fenton, Jr. et al. |
| 2021/0093357 A1 | 4/2021 | Pett et al. |
| 2021/0093358 A1 | 4/2021 | Lindekugel et al. |
| 2021/0113251 A1 | 4/2021 | Vogt et al. |
| 2021/0282812 A1 | 9/2021 | Tierney et al. |
| 2021/0322055 A1 | 10/2021 | Lindekugel et al. |
| 2021/0375445 A1 | 12/2021 | Lindekugel et al. |
| 2021/0393337 A1 | 12/2021 | Zucker |
| 2022/0240976 A1 | 8/2022 | Pett et al. |
| 2022/0249104 A1 | 8/2022 | Pett et al. |
| 2022/0273338 A1 | 9/2022 | Eisenthal et al. |
| 2023/0106545 A1 | 4/2023 | Pett et al. |
| 2023/0285049 A1 | 9/2023 | Howell |
| 2023/0414251 A1 | 12/2023 | Pett et al. |
| 2024/0058036 A1 | 2/2024 | Lindekugel et al. |
| 2024/0261554 A1 | 8/2024 | Akerele-Ale et al. |
| 2024/0277375 A1 | 8/2024 | Lindekugel et al. |
| 2025/0120743 A1 | 4/2025 | Pett et al. |
| 2025/0186085 A1 | 6/2025 | Pett et al. |

FOREIGN PATENT DOCUMENTS

| | | |
|---|---|---|
| EP | 0923961 A1 | 6/1999 |
| EP | 3687024 A1 | 7/2020 |
| ES | 2390297 A1 | 11/2012 |
| FR | 2581548 A1 | 11/1986 |
| JP | 2018509969 A | 4/2018 |
| KR | 20090006621 A | 1/2009 |
| WO | 1997024151 A1 | 7/1997 |
| WO | 1998052638 A3 | 2/1999 |
| WO | 05041790 A2 | 5/2005 |
| WO | 2005046769 A2 | 5/2005 |
| WO | 2005053506 A2 | 6/2005 |
| WO | 2005072625 A2 | 8/2005 |
| WO | 2007018809 A2 | 2/2007 |
| WO | 2008002961 A2 | 1/2008 |
| WO | 2008016757 A2 | 2/2008 |
| WO | 2008033871 A2 | 3/2008 |
| WO | 2008033872 A2 | 3/2008 |
| WO | 2008033873 A2 | 3/2008 |
| WO | 2008033874 A2 | 3/2008 |
| WO | 2008054894 A2 | 5/2008 |
| WO | 2008086258 A1 | 7/2008 |
| WO | 2008124206 A2 | 10/2008 |
| WO | 2008124463 A2 | 10/2008 |
| WO | 2008130893 A1 | 10/2008 |
| WO | 2008134355 A2 | 11/2008 |
| WO | 2008144379 A2 | 11/2008 |
| WO | 2009070896 A1 | 6/2009 |
| WO | 2010043043 A2 | 4/2010 |
| WO | 2011070593 A1 | 6/2011 |
| WO | 2011097311 A2 | 8/2011 |
| WO | 2011139294 A1 | 11/2011 |
| WO | 2013003885 A2 | 1/2013 |
| WO | 2013009901 A2 | 1/2013 |
| WO | 2013173360 A1 | 11/2013 |
| WO | 2014075165 A1 | 5/2014 |
| WO | 2014142948 A1 | 9/2014 |
| WO | 2014144239 A1 | 9/2014 |
| WO | 2014144262 A1 | 9/2014 |
| WO | 2014144489 A2 | 9/2014 |
| WO | 2014144757 A1 | 9/2014 |
| WO | 2014144797 A1 | 9/2014 |
| WO | 2015061370 A1 | 4/2015 |
| WO | 2015177612 A1 | 11/2015 |
| WO | 2016033016 A1 | 3/2016 |

(56) References Cited

FOREIGN PATENT DOCUMENTS

| | | | |
|---|---|---|---|
| WO | 16053834 | A1 | 4/2016 |
| WO | 2016085973 | A1 | 6/2016 |
| WO | 2016163939 | A1 | 10/2016 |
| WO | 2018006045 | A1 | 1/2018 |
| WO | 2018025094 | A1 | 2/2018 |
| WO | 2018058036 | A1 | 3/2018 |
| WO | 2018075694 | A1 | 4/2018 |
| WO | 18098086 | A1 | 5/2018 |
| WO | 2018165334 | A1 | 9/2018 |
| WO | 2018165339 | A1 | 9/2018 |
| WO | 2019051343 | A1 | 3/2019 |
| WO | 2019164990 | A1 | 8/2019 |
| WO | 2021011795 | A1 | 1/2021 |
| WO | 2021016122 | A1 | 1/2021 |
| WO | 2021062038 | A1 | 4/2021 |
| WO | 2021062385 | A1 | 4/2021 |
| WO | 2021062394 | A1 | 4/2021 |
| WO | 2022165232 | A1 | 8/2022 |
| WO | 2022170269 | A1 | 8/2022 |
| WO | 2023177634 | A1 | 9/2023 |
| WO | 2024163884 | A1 | 8/2024 |

OTHER PUBLICATIONS

U.S. Appl. No. 17/335,870, filed Jun. 1, 2021 Final Office Action dated Mar. 26, 2024.
U.S. Appl. No. 17/405,692, filed Aug. 18, 2021 Restriction Requirement dated May 10, 2024.
U.S. Appl. No. 18/075,269, filed Dec. 5, 2022 Non-Final Office Action dated Jun. 24, 2024.
U.S. Appl. No. 18/244,730, filed Sep. 11, 2023 Non-Final Office Action dated May 3, 2024.
U.S. Appl. No. 18/385,056, filed Oct. 30, 2023 Non-Final Office Action dated May 9, 2024.
Ekchian Gregory James et al: "Quantitative Methods for In Vitro and In Vivo Characterization of Cell and Tissue Metabolism", Jun. 11, 2018, XP055839281, retrieved from the internet on Sep. 8, 2021 : URL: https://dspace.mit.edu/bitstream/handle/1721.1/117890/1051211749-MIT.pdf?sequence=1&isAllowed=y.
EP 19757667.1 filed Sep. 18, 2020 Extended European Search Report dated Oct. 22, 2021.
EP 20867024.0 filed Apr. 21, 2022 Extended European Search Report dated Aug. 8, 2023.
EP 20868351.6 filed Apr. 21, 2022 Extended European Search Report dated Aug. 10, 2023.
EP 23166984.7 filed Apr. 6, 2023 Extended European Search Report dated Jul. 5, 2023.
PCT/US2019/018828 filed Feb. 20, 2019 International Preliminary Report on Patentability dated Aug. 27, 2020.
PCT/US2019/018828 filed Feb. 20, 2019 International Search Report and Written Opinion dated Jun. 13, 2019.
PCT/US2020/053119 filed Sep. 28, 2020 International Search Report and Written Opinion dated Jan. 5, 2021.
PCT/US2020/052558 filed Sep. 24, 2020 International Search Report and Written Opinion dated Feb. 11, 2021.
PCT/US2020/053135 filed Sep. 28, 2020 International Search Report and Written Opinion dated Dec. 18, 2020.
PCT/US2021/035232 filed Jun. 1, 2021 International Search Report and Written Opinion dated Oct. 19, 2021.
PCT/US2021/046573 filed Aug. 18, 2021 International Search Report and Written Opinion dated Nov. 30, 2021.
PCT/US2021/047378 filed Aug. 24, 2021 International Search Report and Written Opinion dated Nov. 17, 2021.
PCT/US2021/048542 filed Aug. 31, 2021 International Search Report and Written Opinion dated Dec. 9, 2021.
PCT/US2021/049475 filed Sep. 8, 2021 International Search Report and Written Opinion dated Dec. 9, 2021.
PCT/US2021/028114 filed Apr. 20, 2021 International Search Report and Written Opinion dated Jul. 12, 2021.
PCT/US2021/035475 filed Jun. 2, 2021 International Search Report and Written Opinion dated Sep. 17, 2021.
PCT/US2022/014391 filed Jan. 28, 2022 International Search Report and Written Opinion dated Apr. 14, 2022.
PCT/US2022/015686 filed Feb. 8, 2022 International Search Report and Written Opinion dated May 25, 2022.
PCT/US2023/015127 filed Mar. 13, 2023 International Search Report and Written Opinion dated Jun. 26, 2023.
U.S. Appl. No. 17/031,650, filed Sep. 24, 2020 Final Office Action dated Jul. 20, 2022.
U.S. Appl. No. 17/031,650, filed Sep. 24, 2020 Non-Final Office Action dated Jan. 19, 2022.
U.S. Appl. No. 17/031,650, filed Sep. 24, 2020 Notice of Allowance dated Oct. 12, 2022.
U.S. Appl. No. 17/035,272, filed Sep. 28, 2020 Non-Final Office Action dated Mar. 9, 2023.
U.S. Appl. No. 17/035,272, filed Sep. 28, 2020 Notice of Allowance dated Jul. 7, 2023.
U.S. Appl. No. 17/035,272, filed Sep. 28, 2020 Restriction Requirement dated Dec. 9, 2022.
U.S. Appl. No. 17/035,336, filed Sep. 28, 2020 Notice of Allowance dated Jan. 11, 2023.
U.S. Appl. No. 17/035,336, filed Sep. 28, 2020 Restriction Requirement dated Jul. 26, 2022.
U.S. Appl. No. 17/235,134 filed Apr. 20, 2021 Non-Final Office Action dated Jun. 27, 2023.
U.S. Appl. No. 17/235,134 filed Apr. 20, 2021 Notice of Allowance dated Sep. 20, 2023.
U.S. Appl. No. 17/235,134 filed Apr. 20, 2021 Restriction Requirement dated Mar. 7, 2023.
U.S. Appl. No. 17/335,870, filed Jun. 1, 2021 Non-Final Office Action dated Nov. 15, 2023.
U.S. Appl. No. 17/335,870, filed Jun. 1, 2021 Restriction Requirement dated Jul. 25, 2023.
U.S. Appl. No. 17/337,100, filed Jun. 2, 2021 Final Office Action dated Nov. 21, 2023.
U.S. Appl. No. 17/337,100, filed Jun. 2, 2021 Non-Final Office Action dated Jun. 2, 2023.
U.S. Appl. No. 17/337,100, filed Jun. 2, 2021 Notice of Allowance dated Jan. 24, 2024.
U.S. Appl. No. 17/469,613, filed Sep. 8, 2021 Non-Final Office Action dated Jan. 19, 2024.
U.S. Appl. No. 17/469,613, filed Sep. 8, 2021 Restriction Requirement dated Oct. 23, 2023.
U.S. Appl. No. 17/667,291, filed Feb. 8, 2022 Non-Final Office Action dated Aug. 31, 2023.
U.S. Appl. No. 17/667,291, filed Feb. 8, 2022 Restriction Requirement dated May 31, 2023.
U.S. Appl. No. 17/863,898, filed Jul. 13, 2022 Final Office Action dated Nov. 22, 2023.
U.S. Appl. No. 17/405,692, filed Aug. 18, 2021 Non-Final Office Action dated Sep. 6, 2024.
U.S. Appl. No. 17/410,863, filed Aug. 24, 2021 Non-Final Office Action dated Sep. 5, 2024.
U.S. Appl. No. 17/463,324, filed Aug. 31, 2021 Restriction Requirement dated Aug. 8, 2024.
U.S. Appl. No. 18/075,269, filed Dec. 5, 2022 Notice of Allowance dated Sep. 11, 2024.
U.S. Appl. No. 18/244,730, filed Sep. 11, 2023 Final Office Action dated Aug. 8, 2024.
U.S. Appl. No. 18/244,730, filed Sep. 11, 2023 Notice of Allowance dated Oct. 24, 2024.
U.S. Appl. No. 18/385,056, filed Oct. 30, 2023 Notice of Allowance dated Aug. 29, 2024.
U.S. Appl. No. 17/405,692, filed Aug. 18, 2021 Advisory Action dated Feb. 14, 2025.
U.S. Appl. No. 17/405,692, filed Aug. 18, 2021 Final Office Action dated Dec. 4, 2024.
U.S. Appl. No. 17/410,863, filed Aug. 24, 2021 Notice of Allowance dated Dec. 13, 2024.
U.S. Appl. No. 17/463,324, filed Aug. 31, 2021 Final Office Action dated Feb. 18, 2025.

(56) References Cited

OTHER PUBLICATIONS

U.S. Appl. No. 17/463,324, filed Aug. 31, 2021 Non-Final Office Action dated Oct. 30, 2024.
U.S. Appl. No. 17/469,613, filed Sep. 8, 2021 Advisory Action dated Mar. 21, 2025.
U.S. Appl. No. 17/469,613, filed Sep. 8, 2021 Final Office Action dated Dec. 6, 2024.
U.S. Appl. No. 17/587,900, filed Jan. 28, 2022 Non-Final Office Action dated Nov. 14, 2024.
U.S. Appl. No. 17/405,692, filed Aug. 18, 2021 Non-Final Office Action dated Apr. 10, 2025.
U.S. Appl. No. 17/463,324, filed Aug. 31, 2021 Advisory Action dated Apr. 24, 2025.
U.S. Appl. No. 17/463,324, filed Aug. 31, 2021 Non-Final Office Action dated May 23, 2025.
U.S. Appl. No. 17/469,613, filed Sep. 8, 2021 Notice of Allowance dated May 14, 2025.
U.S. Appl. No. 17/587,900, filed Jan. 28, 2022 Final Office Action dated Apr. 17, 2025.
U.S. Appl. No. 18/653,641, filed May 2, 2024 Non-Final Office Action dated Apr. 5, 2025.

\* cited by examiner

INTRAOSSEOUS MODULAR POWER

PRIORITY

This application is a continuation of U.S. patent application Ser. No. 17/667,291, filed Feb. 8, 2022, now U.S. Pat. No. 11,925,361, which claims the benefit of priority to U.S. Provisional Application No. 63/147,119, filed Feb. 8, 2021, each of which is incorporated by reference in its entirety into this application.

BACKGROUND

Many devices, systems, and methods have been developed to for accessing an interior of a bone of a patient, including for such purposes as intraosseous access, drawbacks that can be resolved, remedied, ameliorated, or avoided by certain embodiments described herein. Intraosseous ("IO") access systems are often required to access the medullary cavity of bones of different sizes. In some instances, battery operated IO access systems may run out of power when drilling larger bones. Replacing a battery pack during the drilling process may require disengaging the IO access systems from the patient causing a significant procedural interruption and placing the patient at a greater risk. Having a second modular power source at the ready that may be coupled to the IO access system to extend the duration of the drilling process while the device is engaged with the patient may be logistically advantageous for the clinician and may reduce risk to the patient.

SUMMARY

Disclosed herein is an intraosseous (IO) access system, including an access assembly having a needle configured to drill into bone via rotation of the needle and a driver. The driver includes a housing, a power converter configured to impart rotational power to the needle, a first power source coupled to the power converter, and a second power source selectively coupleable to the driver, where the second power source is configured to be disposed at least partially external to the housing.

The second power source may be a self-contained power source. The power converter may include a gear assembly configured to convert an input rotational speed of an input shaft to an output rotational speed of an output shaft that is different from the input rotational speed.

The driver may be configured to operate with power supplied individually by either the first power source or the second power source. The power converter may be configured for simultaneous coupling with the first power source and the second power source. Simultaneous coupling of the first power source and the second power source with the power converter may provide for extended operational duration of the system. In some embodiments, simultaneous coupling of the first power source and the second power source with the power converter provides for enhanced torque of the needle.

In some embodiments, the first power source is disposed within the housing and the first power source may be replaceable during use. At least one of the first power source or the second power source may be renewable.

In some embodiments, the driver includes a trigger configured to regulate the rotational speed of the needle.

In some embodiments, the first power source is an electrical power source, and the power converter includes an electric motor.

The second power source may also be an electrical power source, and simultaneous coupling of the first power source and the second power source with the power converter may provide for enhanced electrical current supplied to the motor. In some embodiments, the second power source is coupleable to the driver via a wired connection.

In some embodiments, the first power source is at least partially renewable via the second power source.

In some embodiments, the second power source is a mechanical power source.

Disclosed herein also is a method of drilling through a bone. The method includes providing an intraosseous (IO) access system. The IO access system includes an access assembly including a needle configured to drill into bone via rotation of the needle and a driver. The driver includes a housing, power converter configured to impart rotational power to the needle, a first power source coupled to the power converter, the first power source disposed at least partially within the housing, and a self-contained second power source coupleable to the power converter, the second power source disposed external to the housing. The method further includes applying rotational power to the needle and placing the needle in contact with the bone. The method may further include accessing a medullary cavity of the bone.

The method may further include determining that the first power source contains insufficient energy to drill through a cortex of the bone.

The method may further include coupling the second power source to the power converter.

The method may further include adding power supplied by the second power source to power supplied by the first power source.

The first power source may be an electrical power source. In some embodiments, the second power source is an electrical power source, and in alternative embodiments, the second power source is not an electrical power source.

These and other features of the concepts provided herein will become more apparent to those of skill in the art in view of the accompanying drawings and following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal-end portion, or the proximal length of the needle can include the proximal end of the needle; however, the proximal portion, the proximal-end portion, or the proximal length of the needle need not include the proximal end of the needle. That is, unless context suggests otherwise, the proximal portion, the proximal-end portion, or the proximal length of the needle is not a terminal portion or terminal length of the needle.

With respect to "distal," a "distal portion" or a "distal-end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal-end portion, or the distal length of the needle can include the distal end of the needle; however, the distal portion, the distal-end portion, or the distal length of the needle need not include the distal end of the needle. That is, unless context suggests otherwise, the distal portion, the distal-end portion, or the distal length of the needle is not a terminal portion or terminal length of the needle.

In the following description, certain terminology is used to describe aspects of the invention. For example, in certain situations, the term "logic" is representative of hardware, firmware or software that is configured to perform one or more functions. As hardware, logic may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

Unless defined otherwise, all technical and scientific terms used herein have the same meaning as commonly understood by those of ordinary skill in the art.

The present disclosure relates generally to bone penetrating devices, systems, and methods. In particular, certain embodiments disclosed herein can be used for drilling through or otherwise being inserted into or penetrating hard, compact bone tissue (cortical bone) to gain access to soft bone tissue (cancellous bone) or bone marrow. For example, certain embodiments are particularly well suited for use in intraosseous access procedures for at least the reasons discussed herein and/or for reasons that are otherwise apparent from the present disclosure.

For purposes of illustration, much of the disclosure herein pertains to creating a conduit or communication passageway to an interior of a bone structure by drilling through or otherwise penetrating hard, compact bone tissue to gain access to bone marrow or cancellous bone. Once access to an inner region of a bone is achieved, any variety of suitable procedures can be performed, such as, for example, infusion, aspiration, or extraction of bone marrow. Numerous situations can benefit from providing access to an interior of a bone in manners such as disclosed herein, such as, for example, when other methods of accessing a vein with an IV needle are difficult or in emergency situations, such as heart attack, burns, drug overdoses, etc., when rapid access to the vasculature of a patient via an interior of a bone may be desired. Other illustrative, non-limiting examples include bone marrow biopsy or bone marrow aspiration. The present disclosure is not, however, limited to these specific applications.

Certain known systems and methods for providing access to bone interior (e.g., bone marrow) rely on a penetrator assembly that includes an outer penetrator and an inner trocar operable by a drill to penetrate the compact bone to gain access to the bone marrow. In order to initially make contact with the hard bone, it is often necessary to penetrate the skin and tissue that covers the bone. The prior methods use a sharp inner trocar in order to poke, puncture, or otherwise advance through the tissue. However, while the sharp tip of the trocar may be suitable for providing a passage through tissue, it can be suboptimal for initiating the cutting action through hard bone. In some instances, the sharp point effectively spins on the surface of the hard bone until the cutting edges of the trocar can become engaged with the hard bone.

Certain embodiments disclosed herein can be advantageous over at least the prior approaches just discussed. For example, in some embodiments, rather than using a sharp-tipped trocar that extends distally beyond cutting surfaces of the outer penetrator, a specialized needle having a distal cutting tip is used. The needle may be coupled with an obturator that does not extend beyond a distal face of the needle and is not involved in cutting or piercing the skin. The needle itself can have both the ability to cut or slice through the skin to reach bone, and can also readily bore through hard bone to the marrow. The obturator can prevent tissue debris from entering the needle lumen during insertion. These and/or other advantages of various disclosed embodiments will be apparent from the discussion that follows.

Figure 1:
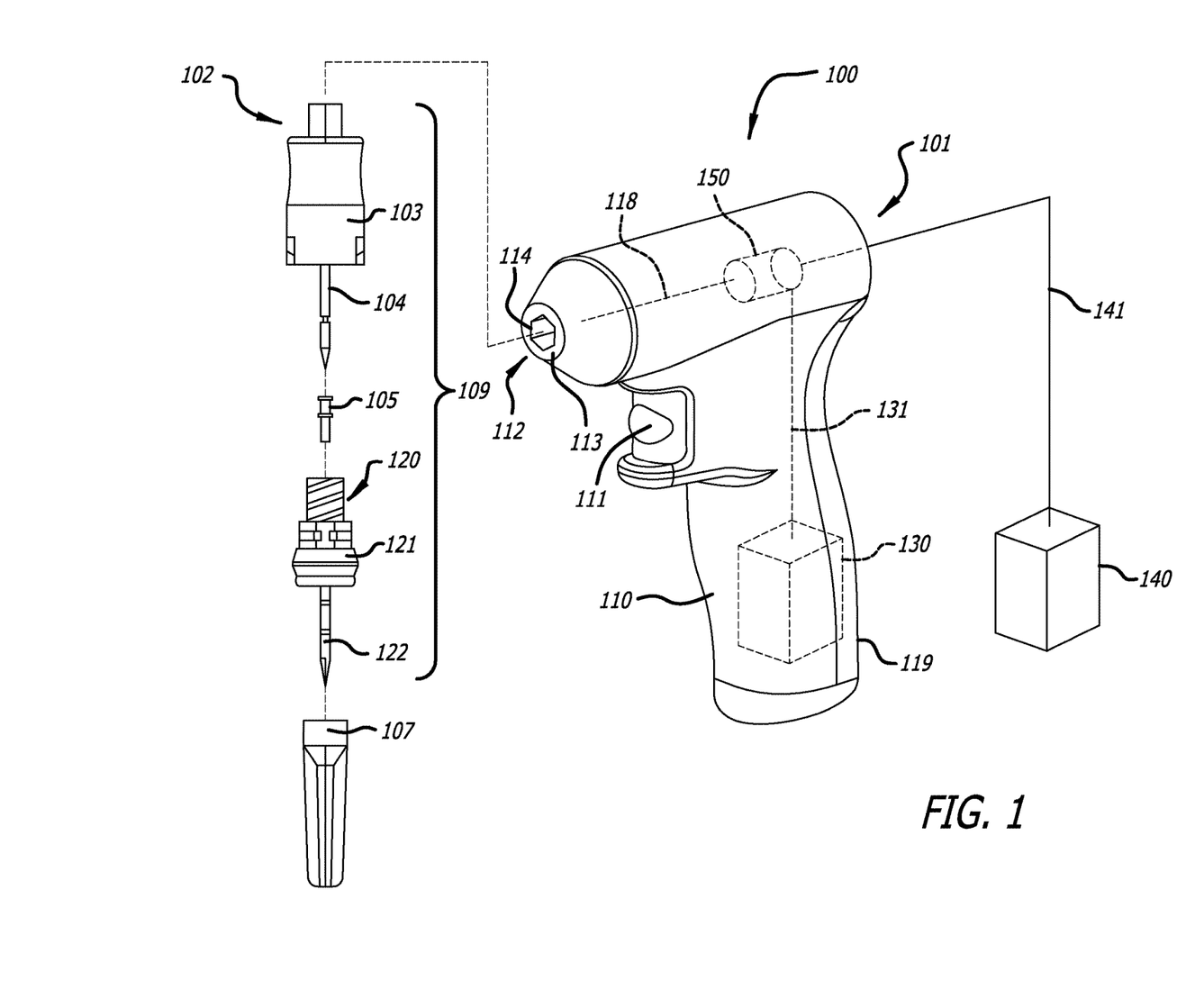
FIG. 1 illustrates an exploded view of an embodiment of an intraosseous access medical device system, wherein an access assembly subset of the system is depicted slightly enlarged and in elevation, and an automated driver component is depicted in perspective, in accordance with some embodiments herein.

FIG. 1 is an exploded view of an embodiment of an intraosseous (IO) access system 100, with some components thereof shown in elevation and another shown in perspective. The IO access system 100 can be used to penetrate skin and underlying hard bone for intraosseous access, such as, for example to access the marrow of the bone and/or a vasculature of the patient via a pathway through an interior of the bone. The process of drilling through the bone may require power from an energy source.

In various embodiments, the system includes a driver 101 and an access assembly 109. The driver 101 can be used to rotate the access assembly 109 into a bone of a patient. In the illustrated embodiment, the system 100 includes a driver 101 which may be automated. For example, the driver 101 can be a drill that achieves high rotational speeds.

The IO access system 100 can further include an obturator assembly 102, a shield 105, and a needle assembly 120, which may be referred to, collectively, as the access assembly 109. The access assembly 109 may also be referred to as an access system. The obturator assembly 102 is referred to as such herein for convenience. In the illustrated embodiment, the obturator assembly 102 includes an obturator 104. However, in various other embodiments, the obturator 104 may be replaced with a different elongated medical instrument. As used herein, the term "elongated medical instrument" is a broad term used in its ordinary sense that includes, for example, such devices as needles, cannulas, trocars, obturators, stylets, etc. Accordingly, the obturator assembly 102 may be referred to more generally as an elongated medical instrument assembly. In like manner, the obturator 104 may be referred to more generally as an elongated medical instrument.

In the illustrated embodiment, the obturator assembly 102 includes a coupling hub 103 that is attached to the obturator 104 in any suitable manner (e.g., one or more adhesives or overmolding). The coupling hub 103 can be configured to interface with the driver 101, as further discussed below. The coupling hub 103 may alternatively be referred to as an obturator hub 103 or, more generally, as an elongated instrument hub 103.

In the illustrated embodiment, the shield 105 is configured to couple with the obturator 104. The coupling can permit relative longitudinal movement between the obturator 104 and the shield 105, such as sliding, translating, or other movement along an axis of elongation (i.e., axial movement), when the shield 105 is in a first operational mode, and can prevent the same variety of movement when the shield 105 is transitioned to a second operational mode. For example, as further discussed below, the shield 105 may couple with the obturator 104 in a manner that permits longitudinal translation when the obturator 104 maintains the shield 105 in an unlocked state, and when the obturator 104 is moved to a position where it no longer maintains the shield in the unlocked state, the shield 105 may automatically transition to a locked state in which little or no translational movement is permitted between the shield 105 and the obturator 104. Stated otherwise, the shield 105 may be longitudinally locked to a fixed or substantially fixed longitudinal orientation relative to the obturator 104 at which the shield 105 inhibits or prevents inadvertent contact with a distal tip of the obturator, as further discussed below. In various embodiments, the shield 105 may be configured to rotate relative to the obturator 104 about a longitudinal axis of the obturator 104 in one or more of the unlocked or locked states.

With continued reference to FIG. 1, the needle assembly 120 is referred to as such herein for convenience. In the illustrated embodiment, the needle assembly 120 includes a needle 122. However, in various other embodiments, the needle 122 may be replaced with a different instrument, such as, for example, a cannula, a tube, or a sheath, and/or may be referred to by a different name, such as one or more of the foregoing examples. Accordingly, the needle assembly 120 may be referred to more generally as a cannula assembly or as a tube assembly. In like manner, the needle 122 may be referred to more generally as a cannula.

In the illustrated embodiment, the needle assembly 120 includes a needle hub 121 that is attached to the needle 122 in any suitable manner. The needle hub 121 can be configured to couple with the obturator hub 103 and may thereby be coupled with the driver 101, as further discussed below. The needle hub 121 may alternatively be referred to as a cannula hub 121.

In the illustrated embodiment, the shield 105 is configured to couple with the needle hub 121. The coupling can prevent relative axial or longitudinal movement between the needle hub 121 and the shield 105, such as sliding, translating, or the like, when the shield 105 is in the first operational mode, and can permit the shield 105 to decouple from the needle hub 121 when the shield 105 is transitioned to the second operational mode. For example, as further discussed below, the shield 105 may couple with the needle hub 121 so as to be maintained at a substantially fixed longitudinal position relative thereto when the obturator 104 maintains the shield 105 in the unlocked state, and when the obturator 104 is moved to a position where it no longer maintains the shield in the unlocked state, the shield 105 may automatically transition to a locked state relative to the obturator 104, in which state the shield 105 also decouples from the needle hub 121.

As further discussed below, the shield 105 can be coupled with the obturator 104, the obturator 104 can be inserted into the needle 122, and the obturator hub 103 can be coupled to the needle hub 121 to assemble the access assembly 109. In the illustrated embodiment, a cap 107 may be provided to cover at least a distal portion of the needle 122 and the obturator 104 prior to use of the access assembly 109. For example, as further discussed below, in the illustrated embodiment, a proximal end of the cap 107 can be coupled to the obturator hub 103.

With continued reference to FIG. 1, the driver 101 may take any suitable form. The driver 101 may include a handle 110 that may be gripped by a single hand of a user. The driver 101 may further include an actuator 111 of any suitable variety via which a user may selectively actuate the driver 101 to effect rotation of a coupling interface 112. For example, the actuator 111 may include a switch or other mechanical or electrical element for actuating the driver 101. The actuator 111 may include a button such as a trigger, as shown. In the illustrated embodiment, the coupling interface 112 is formed as a socket 113 that defines a cavity 114. The coupling interface 112 can be configured to couple with the obturator hub 103. In the illustrated embodiment, the socket 113 includes sidewalls that substantially define a hexagonal cavity into which a hexagonal protrusion of the obturator hub 103 can be received. Other suitable connection interfaces are contemplated.

The driver 101 can include a primary energy (or power) source 130 of any suitable variety that is configured to generate the rotational movement of the coupling interface 112. For example, the primary energy source 130 may provide power in an electrical form (i.e., voltage combined with amperage). In other embodiments, the primary energy source 130 may provide power in a mechanical form (i.e., force combined with velocity or torque combined with rotational speed). In still other embodiments, the primary energy source 130 may provide power in a pneumatic form (i.e., pressure combined with fluid flow).

The driver 101 may include a coupling 131 between the primary energy source 130 and the power converter assembly 150. The coupling 131 is configured to couple the primary energy source 130 to the power converter assembly 150 in any suitable manner consistent with the power from of the primary energy source 130. For example, in the illustrated embodiment, the driver 101 can include an electrical, mechanical, electromechanical, and/or pneumatic coupling 131.

The power converter assembly 150 may be configured to convert a form of power supplied by the primary energy source 130 into rotational power (i.e., torque combined with rotational speed) of the coupling interface 112. For example, the power converter assembly 150 may include a device such as an electrical motor to convert electrical power into rotational power. By way of further example, the power converter assembly 150 may include a gear assembly configured to convert mechanical power supplied by the primary energy source 130 into rotational power of the coupling interface 112. The driver 101 can include a mechanical coupling 118 of any suitable variety to couple the power converter assembly 150 with the coupling interface 112.

Further details and embodiments of the IO access system 100 can be found in WO 2018/075694, WO 2018/165334, WO 2018/165339, U.S. Pat. Nos. 10,893,887, and 10,980, 522, each of which is incorporated by reference in its entirety into this application.

With further reference to FIG. 1, the system 100 further includes a secondary energy (or power) source 240. Similar to the primary energy source 130, the secondary energy source 140 may be electrical, mechanical, or pneumatic. In some embodiments, the primary energy source 130 and the secondary energy source 140 may be similar in some respects. For example, in some embodiments, the primary energy source 130 and the secondary energy source 140 may include the same form of energy, e.g., electrical, mechanical, or pneumatic. In other embodiments, the primary energy source 130 and the secondary energy source 140 may include different forms of energy. For example, in some embodiments, the primary energy source 130 may be electrical and the secondary energy source 140 may be mechanical (e.g., rotational).

Similar to the coupling 131, the driver 101 may include a coupling 141 between the secondary energy source 140 and the power converter assembly 150. The coupling 141 is configured to couple the secondary energy source 140 to the power converter assembly 150 in any suitable manner consistent with the power from of the secondary energy source 140. For example, in the illustrated embodiment, the driver 101 can include an electrical, mechanical, electromechanical, and/or pneumatic coupling 141.

In the illustrated embodiment, the primary energy source 130 may be disposed within a housing 119 or at least partially disposed within the housing 119. In other embodiments, primary energy source 130 me be disposed substantially external to the housing 119 or attached to the housing 119. In some embodiments, the primary energy source 130 may form a portion of the driver 101 or the housing 119 such as the handle 110. By way of contrast, the secondary energy source 140 may be disposed external or substantially external to the housing 119. In some embodiments, the secondary energy source 140 may selectively attached to the driver 101 or coupled to the driver 101 via a tether. The secondary energy source 140 may be coupled to the driver 101 such that power from the secondary energy source 140 may be combined with power from the primary energy source 130 to extend an operating duration of the driver 101. The driver 101 may be configured to operate with power provided only by the primary energy source 130. Similarly, in some embodiments, the driver 101 may be configured to operate with power provided only by the secondary energy source 140.

In some instances of use, the primary energy source 130 may contain insufficient energy to complete the drilling process. The cause for the lack of sufficient energy may be a reduced amount (i.e., less than a full capacity) of energy contained within the primary energy source 130 or the full capacity of the primary energy source 130 may insufficient to drill through a bone of a larger size. In either case, it may be necessary to obtain additional energy to complete the drilling process. In some use instances, the clinician may begin a bone drilling process utilizing power from only the primary energy source 130. Upon an indication that the primary energy source 130 may lack sufficient energy to complete the drilling process, the clinician may connect the secondary energy source 140 to the driver 101, thereby extending the operating duration of the driver 101. In other use instances, the clinician may connect the secondary energy source 140 to the driver 101 before starting the bone drilling process.

In some instances, a substantial portion of the energy contained within the primary energy source 130 and/or the secondary energy source 140 may be expended during a bone drilling process. As such, it may be advantageous to replace the energy expended. In some embodiments, the primary energy source 130 and/or the secondary energy source 140 may be renewable, i.e., energy may be added to (i.e., restored to) the primary energy source 130 and/or the secondary energy source 140.

Figure 2A:
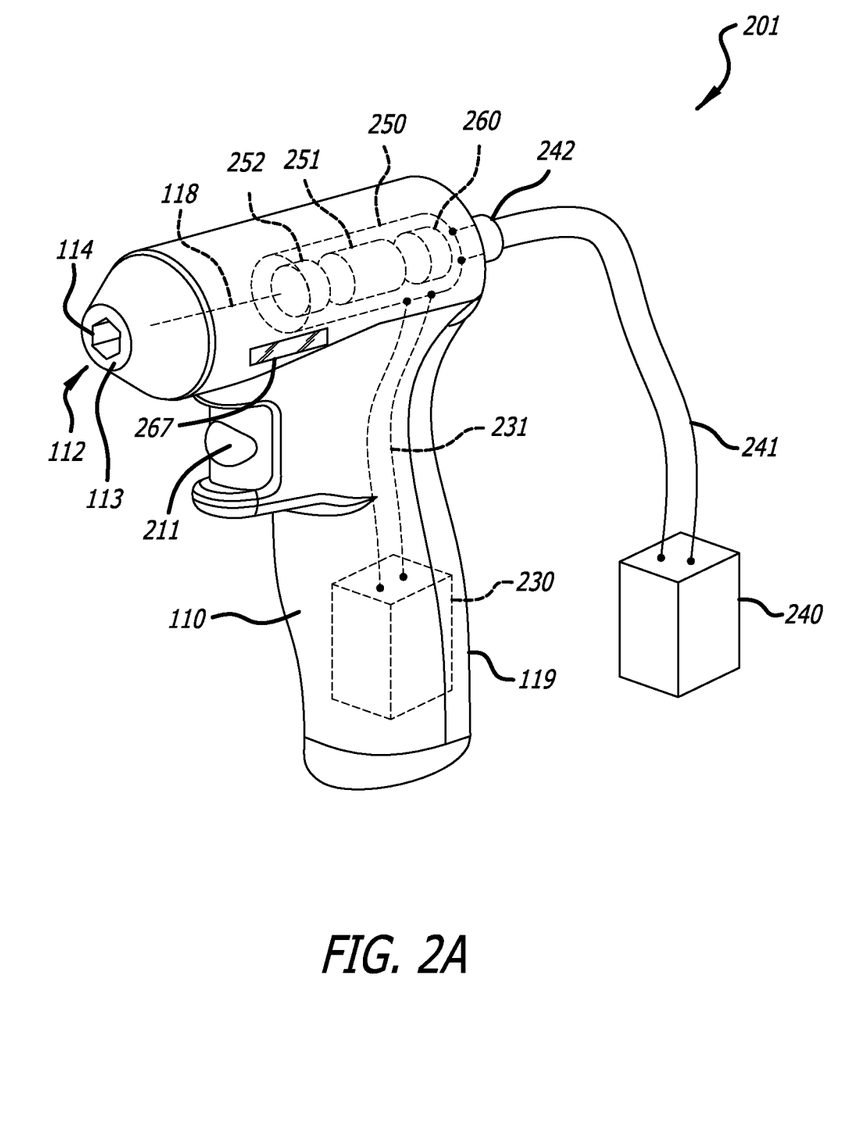
FIG. 2A illustrates a perspective view of an embodiment of an intraosseous driver having an electrical energy source, in accordance with some embodiments.

FIG. 2A is a front perspective view of another embodiment of a driver 201 that can, in certain respects, resemble components of the driver 101 described in connection with FIG. 1, and may be included in the system 100. It will be appreciated that all the illustrated embodiments may have analogous features. Accordingly, like features are designated with like reference numerals, with some reference numerals having leading digits incremented to "2." For instance, the primary energy source is designated as "130" in FIG. 1 and an analogous primary energy source is designated as "230" in FIG. 2A. Relevant disclosure set forth above regarding similarly identified features thus may not be repeated hereafter. Moreover, specific features of the driver 101 and related components shown in FIG. 1 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the driver of FIG. 2A. Any suitable combination of the features, and variations of the same, described with respect to the driver and components illustrated in FIG. 1 can be employed with the driver and components of FIG. 2A, and vice versa. This pattern of disclosure applies equally to further embodiments depicted in subsequent figures and described hereafter.

Referring to FIG. 2A, the driver 210 includes primary and secondary energy sources 230, 240. The primary and secondary energy sources 230, 240 contain energy in the electrical form and provide power to power converter assembly 250 in the electrical form. More specifically, each of the primary and secondary energy sources 230, 240 may include one or more batteries. The primary energy source 230 is coupled to the power converter assembly 250 via electrical conductors 231. Similarly, the secondary energy source 240 is selectively coupleable to the power converter assembly 250 via electrical conductors 241 and a connector set 242. The primary energy source 230 may be disposed within the housing 119 and the secondary energy source 240 may be at least partially disposed external to the housing 119. The connector set 242 may be configured so that the clinician may selectively couple or decouple the secondary energy source 240 with the driver 201.

In the illustrated embodiment, the power converter assembly 250 includes an electric motor 251 configured to convert electrical power into rotational power. In some embodiments, the power converter assembly 250 may include a gear assembly 252 disposed between the electric motor 251 and the coupling 118. In other embodiments, the gear assembly 252 may be omitted.

In some embodiments, the primary energy source 230 and the secondary energy source 240 may be similar in some electrical respects. For example, in some embodiments, the primary energy source 230 and secondary energy source 240 may provide about same voltage. In other embodiments, the primary energy source 230 and secondary energy source 240 may provide different voltages. In some embodiments, the primary energy source 230 and secondary energy source 240 may contain similar amounts of energy when charged. More specifically, the primary energy source 230 and secondary energy source 240 may include the same number of batteries of a similar size. In other embodiments, the primary energy source 230 and secondary energy source 240 may contain different amounts of energy. For example, the secondary energy source 240 may contain about 50 percent, 100 percent, 200 percent or more energy than the primary energy source 230. Alternatively, in some embodiments, the secondary energy source 240 may contain less energy than the primary energy source 230.

In some embodiments, the driver 201 may be connected to an external charger (not shown) to recharge the primary energy source 230. Similarly, the secondary energy source 240 may also be connected to an external charger (not shown) to recharge the secondary energy source 240. In some instances, the driver 201 may be configured such that connecting the secondary energy source 240 to the driver 201 may provide power to the primary energy source 230 to add energy to (i.e., recharge) the primary energy source 230. In some embodiments, the batteries within the one or both of the primary and secondary energy sources 230, 240 may be replaceable by the clinician.

Figure 2B:
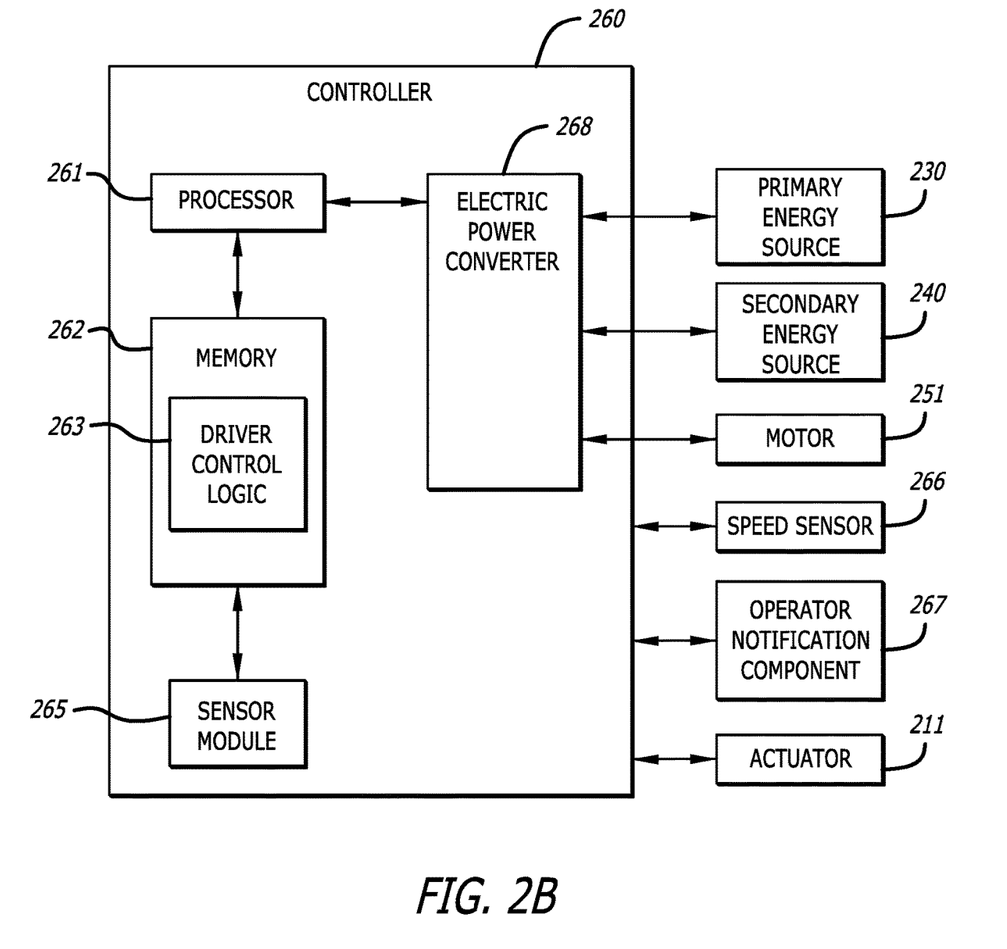
FIG. 2B illustrates a block diagram depicting various elements of the driver of FIG. 2A, in accordance with some embodiments.

FIG. 2B illustrates a block diagram depicting various elements of the driver 101, in accordance with some embodiments. In some embodiments, the driver 101 may include a controller 260 including a processor 261 and memory 262 which may include a non-transitory computer-readable storage medium having driver control logic 263 stored thereon. The controller 260 may also include an electric power converter 268 and a sensor module 265. Each of the primary energy source 230, the secondary energy source 240, and the motor 251 may be coupled to the electric power converter 268. The sensor module 265 may include an ammeter configured to measure an operating amperage draw of the motor 251, and one or more volt meters configured to measure voltages of the primary and secondary energy sources 230, 240. Also coupled to the controller are the actuator 211 and a motor speed sensor 266. The driver 201 may also include an operator notification component 267 coupled to the controller 260. The operator notification component 267 may be configured to provide visual and/or audible indications to the clinician. In some embodiments, the operator notification component 267 may include a display for rendering indicia pertaining to the operation of the driver 201. In some embodiments, the operator notification component 267 may also include an audio device suitable for providing an audible alert to the clinician during operation of the driver 201. The actuator 211 may be configured to provide a binary signal and/or a variable signal to the controller 260. The motor speed sensor 266 provides a variable signal to the controller 260 indicative of the rotational speed of the motor 251.

The electric power converter 268 may be configured to receive power from the primary energy source 230 and the secondary energy source 240 and supply power to the motor 251. In some embodiments, the electric power converter 268 may include a power supply (e.g. a switching power supply) to convert the voltages of the primary energy source 230 and the secondary energy source 240 into an operating voltage for the motor 251. The electric power converter 268 may be coupled to the processor 261 so that the electric power converter 268 may regulate power supplied to the motor 261 according to the driver control logic 263. In some embodiments, the electric power converter 268 may receive power from the secondary energy source 240 and supply power to the primary energy source 230 to recharge the primary energy source 230.

The driver control logic 263 is configured to receive signal data from one or more sensors and control one or more operating characteristics of the driver 201 when executed by the processor 262. In some embodiments, the driver control logic 263 may collect voltage data from the primary energy source 230, where the voltage measurement may indicate a state of charge for the primary energy source 230. The driver control logic 263 may compare the voltage signal with a defined low voltage limit stored in the memory 262. As a result of the comparison, the driver control logic 263 may provide an indication to the clinician via the operator notification component 267 that the remaining energy contained within the primary energy source 230 is below a low limit. In response, the clinician may couple the secondary energy source 240 to the driver 201. In some instances, the clinician may couple the secondary energy source 240 to the driver 201 before starting the drilling process. In other instances, the clinician may couple the secondary energy source 240 to the driver 201 during the drilling process. In some instances, the driver control logic 263 may provide an indication on the operator notification component 267 of a remaining operational duration for the primary energy source 230.

In some embodiments, the driver control logic 263 may collect voltage data from the secondary energy source 240, wherein the voltage measurement may indicate a state of charge for the secondary energy source 240. The driver control logic 263 may compare the voltage signal with a defined low voltage limit stored in memory 262. As a result of the comparison, the driver control logic 263 may provide an indication to the clinician via the operator notification component 267 that the remaining energy contained within the secondary energy source 240 is below a low limit. In response, the clinician may replace the secondary energy source 240 with another secondary energy source 240. In some instances, the clinician may replace the secondary energy source 240 before starting the drilling process. In other instances, the clinician may replace the secondary energy source 240 during the drilling process. In some instances, the driver control logic 263 may provide an indication on the operator notification component 267 of a remaining operational duration for the secondary energy source 240.

The driver control logic 263 may be configured to regulate the rotational speed of the needle. In some embodiments, empirical studies may have determined an optimal rotational speed range for the needle 122 when drilling through bone and the optimal rotational speed range may be stored in the memory 262. The driver control logic 263 may be configured to receive rotational speed data from the speed sensor 266 and compare the speed data with the optimal rotational speed range stored in memory 262. As a result of the comparison, the driver control logic 263 may adjust a voltage or current supplied to the motor 251 to establish and maintain the rotational speed of the needle 122 to be within the optimal rotational speed range. In some instances, the clinician may vary the downward force of the needle 122 on the bone while drilling which may in turn vary the torque load on the needle 122. In such instances, the driver control logic 263 may maintain the rotational speed of needle across a varying torque load on the needle 122.

The driver control logic 263 may be configured provide an indication to the clinician that one or more operating parameters of the driver 201 is outside of a defined range. For example, in some embodiments, empirical studies may have determined a high current limit for efficient use of energy from the primary energy source 230 and/or the secondary energy source 240. In some embodiments, the electrical current data may be related to the torque provided by the motor 251. As such, in some embodiments, the driver control logic 263 may receive electrical current data supplied to the motor 251 from the electrical sensor module 265 and compare the current data with a high current limit stored in the memory 262. As a result of the comparison, the driver control logic 263 may provide a visual and/or audible indication to the clinician via the operator notification component 267. In response, the clinician may reduce an applied force to the needle 122 to reduce the torque on the needle 122 and in turn reduce current supplied to the motor 251.

Figure 3:
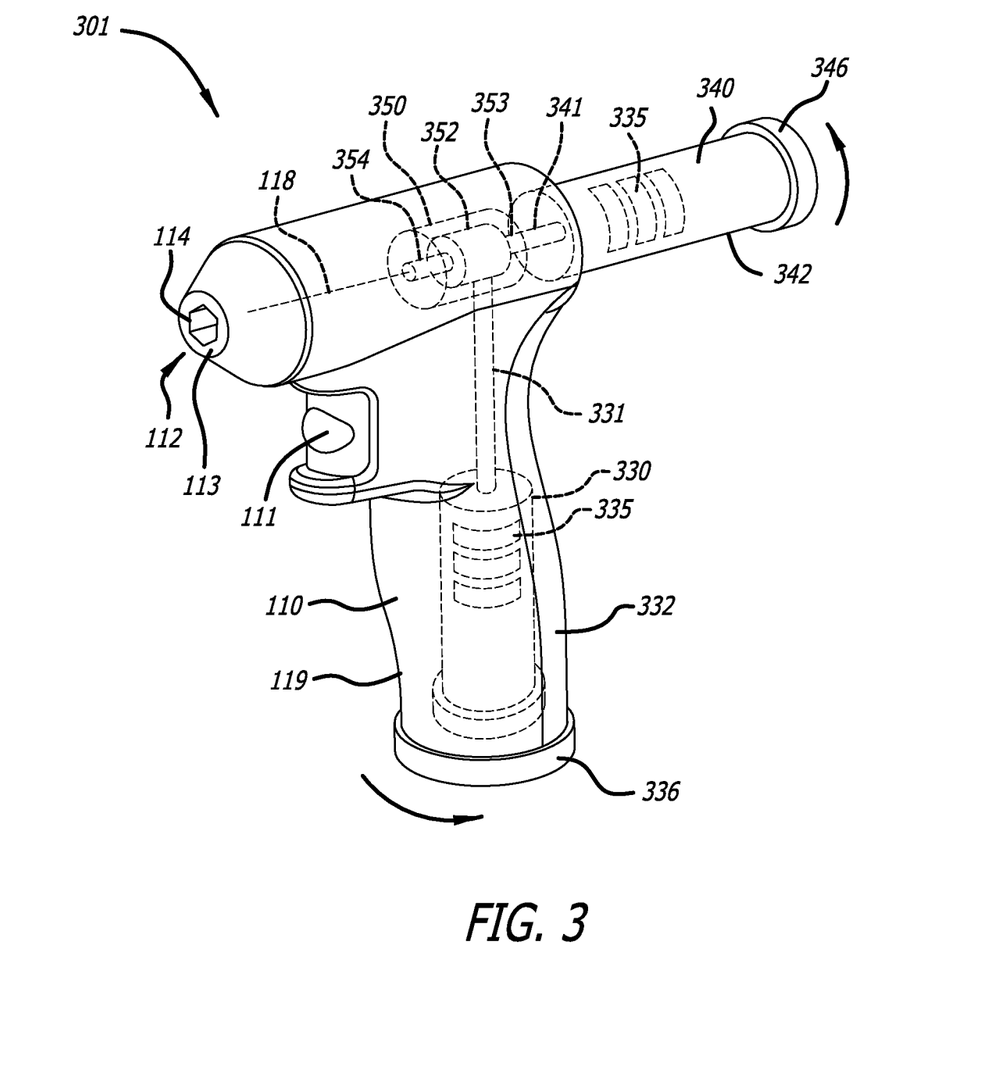
FIG. 3 illustrates a perspective view of another embodiment of an intraosseous driver having a mechanical energy source, in accordance with some embodiments.

FIG. 3 is a front perspective view of another embodiment of a driver 301 that can, in certain respects, resemble components of the driver 101 described in connection with FIG. 1 and may be included in the system 100. Referring to FIG. 3, the primary and secondary energy sources 330, 340 may provide power to the power converter assembly 350 in a mechanical form. More specifically, the primary and secondary energy sources 330, 340 may provide rotational power to the power converter assembly 350. The primary and secondary energy sources 330, 340 may include one or more torsional springs 335 to provide rotational power (i.e., torque in combination with rotational speed) to the power converter assembly 350. In some embodiments, the torsional springs 335 may be coupled together in a series relationship (i.e., end to end) so that the torque supplied by each of the torsional springs 335 is equal. In some embodiments, the torsional springs 335 may be flat torsional springs. The primary energy source 330 is coupled to the power converter assembly 350 via a rotatable shaft 331. Similarly, the secondary energy source 340 is selectively coupleable to the power converter assembly 350 via a rotatable shaft 341. The primary energy source 330 may be substantially disposed within the housing 119 and the secondary energy source 340 may be at least partially disposed external to the housing 119. The driver 301 may be configured to be operational when either or both of the primary and secondary energy sources 330, 340 is coupled to the power converter assembly 350.

The power converter assembly 350 is configured to convert the rotational power from the primary and secondary energy sources 330, 340 into rotational power of the coupling interface 112. In the illustrated embodiment, the power converter assembly 350 includes a gear assembly 352. The gear assembly 352 may be configured to change the orientation of the rotational power. In other words, the gear assembly 352 may receive rotational power via the rotatable shaft 331 disposed in a first orientation into rotational power of the output shaft 354 disposed in a second orientation, wherein the second orientation is disposed at about 90 degrees with respect to the first orientation. The gear assembly 352 may also be configured to change a rotational speed of the output shaft 354 with respect to a rotational speed of the input shaft 353. In some embodiments, the gear assembly 352 may be configured to increase a rotational speed of the output shaft 354 with respect to a rotational speed of an input shaft 353 by a ratio of about 20 to 1, 50 to 1, 100 to 1, 500 to 1, or more so that the rotational speed of the needle 122 is appropriate for drilling through bone.

In some embodiments, the primary energy source 330 and the secondary energy source 340 may be similar in some respects. For example, in some embodiments, the primary energy source 330 and secondary energy source 340 may interchangeable. In some embodiments, the primary energy source 330 and secondary energy source 340 may contain similar amounts of energy when disposed in a wound-up state. More specifically, the primary energy source 330 and secondary energy source 340 may include the same number of torsional springs 335 of a similar size. In other embodiments, the primary energy source 330 and secondary energy source 340 may contain different amounts of energy. For example, the secondary energy source 340 may contain about 50 percent, 100 percent, 200 percent, or more energy than the primary energy source 330. Alternatively, in some embodiments, the secondary energy source 340 may contain less energy than the primary energy source 330.

The primary energy source 330 may be renewed from a lesser wound-up state to a greater wound-up state. The primary energy source 330 may include a rewind knob 336 coupled to the torsional springs 335. The primary energy source 330 is configured such that turning the rewind knob 336 with respect to a housing 332 of the primary energy source 330 winds up the torsional springs 335 thereby restoring energy to the primary energy source 330. As shown in FIG. 3, the rewind knob 336 may extend beyond the handle 110 making the rewind knob 336 accessible to the clinician when the primary energy source 330 is disposed within the housing 119. As such, the clinician may turn the rewind knob 336 with respect to the handle 110 to wind up the torsional springs 335.

Similarly, the secondary energy source 340 may be renewed from a lesser wound-up state to a greater wound-up state. The secondary energy source 340 may include a rewind knob 346 coupled to the torsional springs 335 so that turning the rewind knob 346 with respect to a housing 342 of the secondary energy source 340 winds up the torsional springs 335 thereby restoring energy to the secondary energy source 340.

Figure 4:
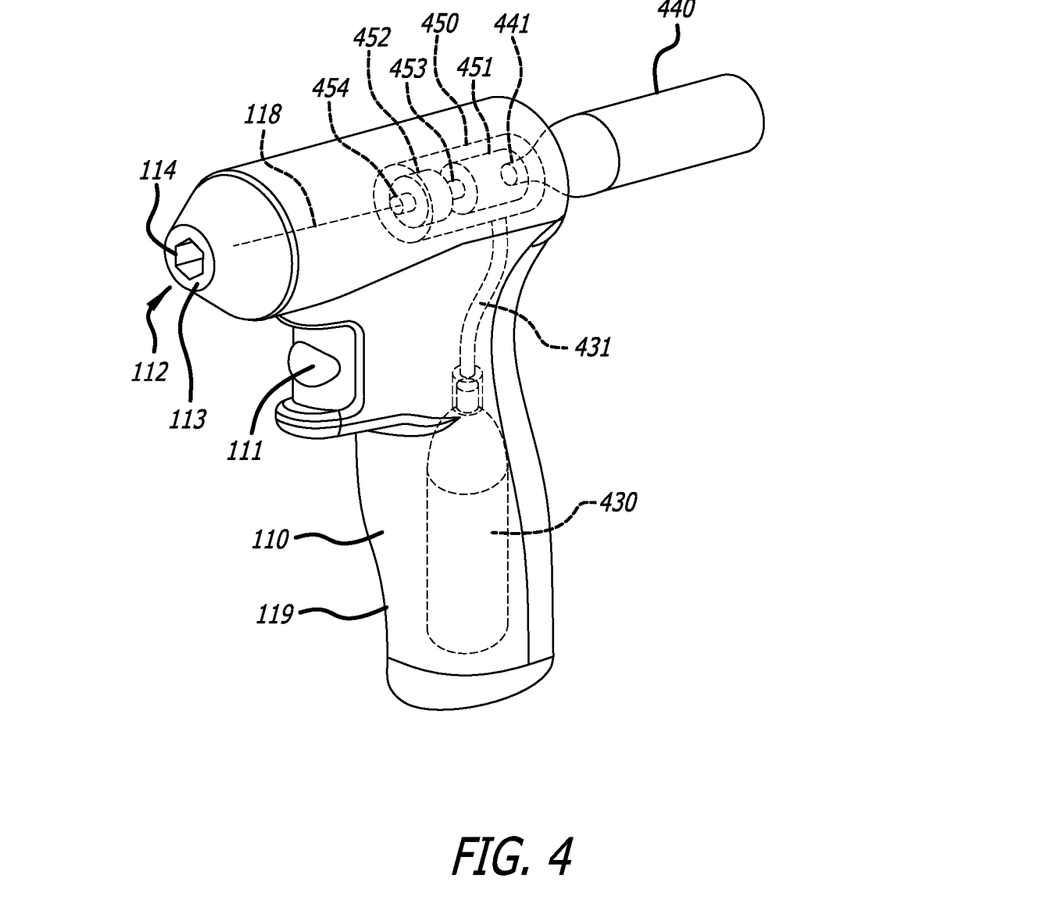
FIG. 4 illustrates a perspective view of another embodiment of an intraosseous driver having a pneumatic energy source, in accordance with some embodiments.

FIG. 4 is a front perspective view of another embodiment of a driver 401 that can, in certain respects, resemble components of the driver 101 described in connection with FIG. 1 and may be included in the system 100. Referring to FIG. 4, the primary and secondary energy sources 430, 440 may provide power to the power converter assembly 450 in a pneumatic form. Each of the primary and secondary energy sources 430, 440 may include a pressurized fluid cartridge (e.g. a CO2 cartridge) to provide pneumatic power (i.e., pressure in combination with fluid flow) to the power converter assembly 450. The primary energy source 430 is coupled to the power converter assembly 450 via a fluid conduit 431. Similarly, the secondary energy source 440 is selectively coupleable to the power converter assembly 450 via a fluid conduit 441. The primary energy source 430 may be substantially disposed within the housing 119 and the secondary energy source 440 may be at least partially disposed external to the housing 119. The driver 401 may be configured to be operational when either or both of the primary and secondary energy sources 430, 440 is coupled to the power converter assembly 450.

In the illustrated embodiment, the power converter assembly 450 includes an air turbine 451 to convert pressurized fluid flow into rotational power of a turbine output shaft 453. In other embodiments, the power converter assembly 450 may include a vane pump, a piston pump, or any other suitable mechanism for converting pressurized fluid flow into rotational power. The power converter assembly 450 may also include gear assembly 452. The gear assembly 452 may be configured to reduce a rotational speed of a gear-assembly output shaft 454 with respect to a rotational speed of the turbine output shaft 453 by a ratio of about 2 to 1, 5 to 1, 10 to 1, 50 to 1, 100 to 1, or more so that the rotational speed of the needle 122 is appropriate for drilling bone.

In some embodiments, the primary energy source 430 and the secondary energy source 440 may be similar in some respects. For example, in some embodiments, the primary energy source 430 and secondary energy source 440 may interchangeable. In some embodiments, the primary energy source 430 and secondary energy source 440 may contain similar amounts of pneumatic energy. More specifically, the primary energy source 430 and secondary energy source 440 may include a cartridge of about the same volume containing a similar mass of fluid. In other embodiments, the primary energy source 430 and secondary energy source 440 may contain different amounts of energy. For example, the secondary energy source 440 may contain about 50 percent, 100 percent, 200 percent or more energy than the primary energy source 430. Alternatively, in some embodiments, the secondary energy source 440 may contain less energy than the primary energy source 430. Either or both of the primary and secondary energy sources 430, 440 may be replaceable by the clinician.

Some embodiments of the system 100 may be configured to include components of any of the drivers 201, 301, and 401. For example, an embodiment of the system 100 may include the driver 201 having the electrical primary energy source 230 combined with the rotational secondary energy source 340 or the pneumatic secondary energy source 440. Embodiments of the system 100 that include other combinations of drivers and secondary energy sources are also contemplated.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

In an exemplary method of the use, the clinician may obtain the system 100. The clinician may further apply rotational power to the needle by pressing the actuator 111 (trigger). The clinician may then contact the needle 122 with the bone to drill through the bone. At some point before or during the drilling procedure, the clinician may determine that the first energy source 130 contains insufficient energy to complete the drilling procedure. In some embodiments, the system 100 may visually or audibly notify the clinician that the first energy source 130 contains insufficient energy. As a result of the determination, the clinician may couple the second energy source 140 to the driver 101 so that power from the second energy source 140 is combined with power from the first energy source 130. In some embodiments, the first power source 130 is an electrical power source and the second power source 140 is an electrical power source. In other embodiments, the first power source 130 is an electrical power source and the second power source 140 is not an electrical power source.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An intraosseous access system, comprising:
    a needle configured to drill into bone via rotation;
    a driver configured to impart rotational power to the needle, the driver containing a power converter and a first power source connected to the power converter; and
    a second power source external to the driver, the second power source configured for selective connection directly to the power converter in the driver to assist in imparting rotational power to the needle during use of the intraosseous access system.

2. The intraosseous access system according to claim 1, wherein the second power source is a self-contained power source.

3. The intraosseous access system according to claim 1, wherein the power converter comprises a gear assembly configured to convert an input rotational speed of an input shaft to an output rotational speed of an output shaft that is different from the input rotational speed.

4. The intraosseous access system according to claim 1, wherein the driver is configured to operate with power supplied either simultaneously by the first power source and the second power source or individually by the first power source or the second power source.

5. The intraosseous access system according to claim 1, wherein combining power from the first power source and the second power source provides for an extended operational duration of the intraosseous access system and enhanced torque of the needle.

6. The intraosseous access system according to claim 1, wherein the first power source is replaceable during use.

7. The intraosseous access system according to claim 1, wherein at least one of the first power source or the second power source is renewable.

8. The intraosseous access system according to claim 1, wherein the driver further comprises a trigger configured to regulate a rotational speed of the needle.

9. The intraosseous access system according to claim 1, wherein the first power source is an electrical power source, and wherein the power converter comprises an electric motor.

10. The intraosseous access system according to claim 1, wherein the second power source is an electrical power source.

11. The intraosseous access system according to claim 10, wherein the second power source is configured for connection to the driver via a wired connection.

12. The intraosseous access system according to claim 10, wherein the first power source is at least partially renewable via the second power source.

13. The intraosseous access system according to claim 1, wherein the second power source is a mechanical power source.

14. A method for drilling through a bone, comprising:
providing an intraosseous access system comprising:
a needle configured to drill into the bone via rotation;
a driver configured to impart rotational power to the needle, the driver containing a power converter and a first power source connected to the power converter; and
a second power source external to the driver, the second power source configured for selective connection directly to the power converter in the driver to assist in imparting rotational power to the needle during use of the intraosseous access system;
applying rotational power to the needle with the second power source disconnected from the driver; and
placing the needle in contact with the bone.

15. The method according to claim 14, further comprising accessing a medullary cavity of the bone.

16. The method according to claim 14, further comprising:
determining that the first power source contains insufficient energy to drill through a cortex of the bone,
connecting the second power source to the driver, and
drilling through the cortex of the bone.

* * * * *